United States Patent
Weisbart (12)

(10) Patent No.: US 6,232,444 B1
(45) Date of Patent: *May 15, 2001

(54) CONSERVED ANTI-DNA ANTIBODY IDIOTYPE ASSOCIATED WITH NEPHRITIS IN MURINE AND HUMAN LUPUS

(75) Inventor: Richard Weisbart, Los Angeles, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/629,355

(22) Filed: Apr. 8, 1996

Related U.S. Application Data

(63) Continuation of application No. 07/471,880, filed on Jan. 29, 1990, now abandoned.

(51) Int. Cl.[7] ............................................. C07K 16/42
(52) U.S. Cl. ............... 530/387.2; 435/327; 530/387.3; 530/868
(58) Field of Search .................... 435/7.9, 7.95, 435/965, 327; 436/508, 548; 530/387.2, 868, 387.3; 424/131.1, 140.1

(56) References Cited

U.S. PATENT DOCUMENTS

| | | | |
|---|---|---|---|
| 4,692,416 | 9/1987 | Diamond | 436/548 |
| 4,812,397 | 3/1989 | Weisbart | 435/7 |
| 4,816,567 * | 3/1989 | Cabilly et al. | 530/387.3 |
| 4,865,841 * | 9/1989 | Balint, Jr. et al. | 424/140.1 |

OTHER PUBLICATIONS

Herbert et al, Dictionary Of Immunology—3rd Ed., Blackwell Scientific Publications, p. 199, 1985.*

Weisbart et al., Arth, Rheum., 30 (4 Suppl.), S104, 1987.

Hahn et al., Journ. Immunol., 138, 2110–2119, 1987.

Livneh et al., Journ. Immunol., 138, 123–127, 1987.

Riott, Essential Immunology, Scientific Publications, Oxford UK, 1984, pp. 14–15, 5th Ed., Blackwell.

R.H. Weisbart et al., J. Immunol., 144, 2653–2658, 1990.

W.J. Herbert et al. (Eds.), Dictionary of Immunology, 3d Ed., Blackwell Sci. Pub., 1985, p. 106.

Dierksheide, ASM News, 53, 677–680, 1987.

Kalunian et al., Arth. & Rheum., 32, 513–522, 1989.

* cited by examiner

*Primary Examiner*—David Saunders
(74) *Attorney, Agent, or Firm*—Gray Cary Ware & Freidenrich LLP; Lisa A. Haile

(57) ABSTRACT

Methods and antibody compositions are provided for the diagnosis and treatment of lupus nephritis. By employing B-cells of a lupus nephritis host with a fusion partner, antibodies can be obtained, which may serve as immunogens for the production of antiidiotypic antibodies, which may then be used for diagnosis and therapy of lupus nephritis.

6 Claims, No Drawings

CONSERVED ANTI-DNA ANTIBODY IDIOTYPE ASSOCIATED WITH NEPHRITIS IN MURINE AND HUMAN LUPUS

This is a continuation of application Ser. No. 07/471,880 filed on Jan. 29, 1990 and now abandoned.

TECHNICAL FIELD

The field of this invention is the diagnosis and treatment of nephritis associated with systemic lupus erythematosus.

BACKGROUND

Antibodies to deoxyribose nucleic acid (DNA) are the hallmark of systemic lupus erythenotesus (SLE) and are associated with the development of kidney disease (nephritis). However, anti-DNA antibodies are heterogeneous and the structural basis for pathogenic anti-DNA antibodies has remained elusive. Idiotypes are structural determinants on or near antibody binding sites recognized by a second (antiidiotype) antibody. Antiidiotype antibodies can be used to identify unique structural features of potentially pathogenic anti-DNA antibodies. Although several anti-DNA antibody antiidiotypes have been produced, an anti-idiotype has not been produced that characterizes unique structural features of anti-DNA antibodies that are conserved in both murine and human lupus associated with nephritis.

Because of the substantial interest in being able to diagnose and treat lupus associated with nephritis, various efforts have been made to determine the causative agent of nephritis associated lupus and to find therapeutic techniques. It is therefore of interest to be able to develop antibodies which are capable of recognizing disease related anti-DNA antibodies.

RELEVANT LITERATURE

References describing the relationship between anti-DNA antibodies, systemio-lupus erythematosus and development of kidney disease are Koffler et al., *J. Exp. Med.* 134, 294 (1971); Miller et al., *Arthritis Rheum.* 24, 602 (1981), Koffler et al., *J. Exp. Med.* 126, 607 (1967); Koffler, *Annu. Rev. Med.* 25, 149 (1974); Tron and Bach, *Clin. Exp. Immunol.* 28, 426 (1977). Articles describing anti-DNA antibody antiidiotypes are Rauch et al., *J. Immunol.* 129, 236 (1982); Isenberg et. al., Lancet 2, 417 (1984), Hahn and Ebling, *J. Immunol.* 138, 2110 (1987); Livneh et al., *J. Immunol.* 138, 123 (1987).

MRL-lpr/lpr mice are known to develop severe nephritis resulting in death (Theofilopoulos and Dixon, Adv. Immunol. 37, 269 (1985); Dixon, *Arthritis Rheum.* 28, 1081 (1985).

SUMMARY OF THE INVENTION

Methods and compositions are provided for inducing an immune response for protection against diseases where an idiotype is expressed and related to the disease, e.g., lupus nephritis, and for diagnosis and treatment of such diseases. Particularly, monoclonal antibodies are provided which may serve as vaccines and for diagnosis and treatment of such diseases.

DESCRIPTION OF SPECIFIC EMBODIMENTS

Methods and compositions are provided associated with the treatment and diagnosis of diseases where antibodies are produced where the idiotype is diagnostic of the disease and can be used as an immunogen for inducing immune protection. Diseases of particular interest include lupus nephritis and B-cell lymphomas. For lupus nephritis, the monoclonal antibodies are directed to binding to double stranded DNA (dsDNA) or monoclonal antibodies which specifically bind to an idiotype associated with antibody binding to dsDNA, which is also associated with lupus nephritis. By employing particular variable regions of antibodies which bind to dsDNA as an immunogen, a mammalian host may be immunized for protection against lupus nephritis or may be used to produce antibodies which can provide for diagnosis of the presence of antibodies associated with lupus nephritis or therapeutic treatment of lupus nephritis.

Lupus nephritis may be associated with a wide variety of mammalian hosts, including murine, primate, particularly human, especially women. To obtain monoclonal antibodies specific for binding to dsDNA, one may employ lymphocytes from a host suffering from the disease. The lymphocytes may be splenocytes, lymphocytes from tonsils or lymph nodes, peripheral blood lymphocytes, or the like.

The lymphocytes from the host may be immortalized by any convenient means, e.g., fused with any convenient fusion partner for production of hybridomas in accordance with conventional techniques. Various techniques may be employed for immortalizing B-lymphocytes producing desired antibodies, using myeloid cells, heteromyelomas, Epstein-Barr virus infection, FOX-NY myeloid cells, etc. The resulting cells may then be cloned by limiting dilution and screened for production of the desired antibodies. Conveniently, DNA, e.g., calf thymus DNA may be used as the ligand for screening and any convenient assay technique for detecting complex formation between the DNA and the antibody may be employed. Assays which may be used include ELISA, RIA or the like. Other characteristics of the antibody may be binding to single stranded DNA (ssDNA) and poly dT, but may also include poly dA, poly dC, poly dG or cardiolipin.

An antibody of particular interest was designated mAb 3E10 which is Characterized as an IgG 2a kappa with an isoelectric point of about pH 7.5 to 8.

Antibodies having these characteristics may be used as immunogens for producing antiidiotypes, either as a vaccine, or for the production of antibodies for use in therapy and diagnosis. The entire antibody need not be used, only the variable region is required or even either the light or heavy chain variable region.

Immunization may be achieved in any conventional manner, by immunizing the host, particularly with an adjuvant. Various adjuvants include BCG, aluminum hydroxide, monophosphoryl lipid A, trehalose 6,6'- dimycolate, etc. In addition, the antibody or fragment thereof may be conjugated with various carriers, such as keyhole limpet hemocyanin, tetanus toxoid, gamma globulin, etc.

Antiidiotype monoclonal antibodies may then be produced as described previously. The resulting antiidiotype monoclonal antibodies thus produced should show specific binding to the idiotype of the dsDNA binding antibody. These antibodies may be further screened to demonstrate binding to antibodies present in a host having lupus nephritis. Desirably, the antiidiotype antibody should be at least about 25% inhibited from binding by the presence of the DNA ligand. Furthermore, the antibody will normally remove at least 10%, usually at least 15% of the total antibody binding to dsDNA in a lupus nephritis diseased host.

Depending upon the application, syngeneic, allogeneic, or xenogeneic antibodies may be employed. Chimeric antibodies may be used, where the variable region may be from one host and the constant region from the host to be treated. Antibody fragments may be employed, such as $F(ab')_2$, $F(ab')$, recombinant $F_v$, or the like, where the fragment is free of the constant region. The important factor in the case of therapy is to provide effective binding to endogenous antibodies associated with lupus nephritis.

The antibodies may be administered in any convenient form, particularly parenteral, more particularly intravascularly or subcutaneously. The antibodies or fragments thereof will be administered in an effective amount in a physiologically acceptable medium, such as water, PBS, saline, aqueous ethanol, or the like. The amount administered will generally be in the range of about 10 mg/kg to 50 mg/kg.

One antibody of particular interest is referred to as mAb 1C7. This antibody is a murine IgG 2b antibody and is specific for an idiotype or anti-DNA antibodies. The antibodies may be murine, e.g., rat or mouse, lagomorph, bovine; equine, primate, e.g., monkey, gorilla, human, etc., ovine, porcine, etc. The antibody may be cross reactive with cell membrane determinants and serve as a diagnostic for the presence of such determinants.

The cells producing the desired antibodies may be used as a source of DNA or mRNA for production of cDNA to provide the sequence for the variable region. By employing known techniques, the genes may be isolated. Techniques include sequencing a portion of the protein and preparing redundant probes encoding for the particular sequence. These probes may then be used to screen the genomic or cDNA library from the host cell. Alternatively, one may use subtraction libraries, where a cDNA library from a pre-B cell may be used to subtract from a library from the host cell expressing the desired monoclonal antibody. The particular manner in which the DNA is identified is not critical to this invention.

The sequence may then be manipulated to provide for only the variable region of the heavy and/or light chain, as separate subunits or as a single subunit, the variable region from the light and heavy chains may be joined to constant regions of light and heavy chains to provide for chimeric antibodies, or the like. See for example, EPA 0 173 494.

For use in diagnosis, the antiidiotype antibody may be employed in any of a variety of assays. Either the antiidiotypic antibody may be labeled, or an antibody to the anti-idiotypic antibody may be labeled. Assays may be homogeneous or heterogeneous and include various commercially available assays, such as RIA, ELISA, EMIT, CEDIA, sandwich assays, etc. Labels which may be employed include radioisotopes, enzymes, fluorescers, particles, etc. The particular manner in which the antibodies are detected is not critical to this invention. Conveniently, a blood sample is employed and contacted with monoclonal antiidiotype antibody bound to a surface. Anti-DNA antibodies with the DNA specific idiotype may then be detected with labeled antisera specific for human immunoglobulin.

For other diseases, the same approach may be employed, where the idiotype of the immunoglobulin of the B-cell lymphoma or antibody to the B-cell lymphoma may serve as the antibody of interest and the immunogen for producing the antiidiotype. Thus, the antibodies may serve in diagnostic and therapeutic approaches.

The following examples are offered by way of illustration and not by way of limitation.

EXAMPLES

Anti-DNA and (antiidiotype) antibodies in serum of MRL-lpr/lpr mice immunized with mAb3E10.

Monoclonal anti-DNA were produced by fusing spleen cells from two female MRL-lpr/lpr mice with FOX-MY myeloma cells as previously described (Taggart and Samloff, *Science* 219, 1228 (1982)). Cell culture supernatants were assayed for antibodies to calf thymus DNA by an enzyme-linked immunosorbent assay (ELISA).

Only three of 960 clones produced monoclonal antibodies to dsDNA. Only 1 monoclonal antibody mAb3E10 bound equally well to single stranded DNA and dsDNA and also bound poly dT, but not poly dA, poly dC, poly dG or cardiolipin. mAb3E10 was cloned four times by limiting dilution and produced in large amounts as ascites in Balb/c mice, and purified from ascites by elution from immobilized protein A. mAb3E10 was characterized as an IgG 2a kappa with an isoelectric point of about pH 7.5 to 8.0.

Thirteen mice were immunized subcutaneously each week with 50 µg of mAb3E10 conjugated with an equivalent weight of keyhole limpet hemocyanin in the presence of glutaraldehyde as previously described. Garvey et al., *Methods in Immunology*, Addison-Wesley Publishing Co., p.263 (1977). Complete Freund's adjuvant was used for the initial immunization and incomplete Freund's adjuvant was used for subsequent immunizations.

Microtiter plates of polystyrene were coated with poly-L-lysine and then with calf thymus DNA (10 µg/ml in Tris-HCl, pH 7.3) previously denatured by heating to 100° C. and cooling rapidly in an ice bath. Microtiter plates were coated similarly with lambda phage extracted with phenol. $F(ab')_2$ fragments of mAb 3E10 were prepared by pepsin digestion, (Kaminski et al., J. Immunol. 138, 1289 (1987)) and passed through a column of protein-A sepharose (Pharmacia, Inc., Piscataway, N.J.) to remove Fc fragments and undigested immunoglobulin. Microtiter wells were coated with Mab3E10 $F(ab')_2$ fragments (10 µg/ml in sodium carbonate buffer, pH 9.6). Mouse serum was assayed for ntibodies to ssDNA, dsDNA and mAb3E10 by incubating overight at 4° C. serum diluted 1:100 in 0.15 M phosphate buffered saline, pH 7.2 containing heat-inactivated fetal calf serum. The plates were washed, and mouse IgG was detected using peroxidase conjugated goat antibodies specific for the Fc fragment of mouse IgG. Bound peroxidase was determined by the conversion of 2,2-azino-di-ethyl-benzthiazolinesulfonate (ABTS) to a chromophore with an optical density (absorbance) maxima at 414 nm.

Mice were immunized with mAb3E10 as follows: 50 µg of antibody conjugated with an equal weight of KLH were injected subcutaneously once each week. Freund's Complete Adjuvant was used for the first injection, and Freund's Incomplete Adjuvant was used for subsequent injections. Survival at 6 months of age of mice immunized with mAb3ElO (10/13 alive) was significantly greater than mice immunized with KLH 2/14 alive) ($x^2$=8.3, p=0.004) or normal mouse IgG (5/15 alive) ($x^2$=3.7, p=0.05). Moreover, 9 of the 10 surviving mice immunized with mAb3E10 appeared entirely normal in marked contrast to all of the control animals which showed signs of wasting and lymphadenopathy and most had loss of facial hair and whiskers. There was less impairment of renal function at 6 months of age in mice immunized with mAb3E10 as shown by a lower mean blood urea nitrogen (BUN) (30.8±4.9 mg/dL,N=10) than the control group (41.6±13.5 mg/dL, N−7;F=5.47, p=0.034 by ANOVA); normal levels of BUN in 10 normal Balb/c mice were 30.0±7.5 mg/dL. Mice were sacrificed at 6 months of age for histopathologic studies of the kidneys. Glomeruli of mice immunized with mAb3E10 showed only mild hypercellular changes compared to the severe inflammatory and proliferative changes involving the glomeruli in the control mice. Immunization with mAb3E10 suppressed serum antibodies to dsDNA but not to ssDNA compared to control animals at 6 months of age. In addition, immunization with mAb3E10 stimulated the production of antiidiotype antibodies that bound F(ab')$_2$ fragments of mAb3E10.

Spleen cells from two mice immunized with mAb3E10 were fused with FOX-NY cells, and hybrids were screened for antiidiotype antibodies that bound F(ab')$_2$ fragments of mAb3E10. One positive clone (mAb1C7) was identified in 1,700 hybrids, and it was cloned four times by the method of limiting dilution. mAb1C7 was characterized as an IgG 2b, produced in large amounts as ascites, and purified as described for mAb3E10. mAb1C7 bound mAb3E10 and other monoclonal anti-dsDNA antibodies, but it did not bind human serum albumin, normal mouse IgG, human IgG Fc fragments, and monoclonal antibodies that did not bind DNA. The idiotype on mAb3E10 recognized by mAb 1C7 was designated the DNA specific (DNAsp) idiotype, since it was found predominantly in association with anti-DNA antibodies. mAb1C7 was used to demonstrate the absence of the DNAsp idiotype in serum of 2 month old MRL-lpr/lpr mice before they developed anti-DNA antibodies. In contrast the DNAsp idiotype was present in serum of MRL-lpr/lpr mice at 6 months of age when there were elevated levels of anti-DNA antibodies. The binding of mAb1C7 to mAb3E10 was inhibited 50% by only 0.25 μg/ml of soluble DNA, indicating that mAb1C7 bound mAb3E10 within or near the binding site for DNA. mAb1C7 was purified from ascites by binding to and elution from protein A. Microtiter plates were coated with purified mAb1C7 (10 μg/ml) overnight at 4° C. and serum (100 μl diluted 1:100 PBST containing 1% ovalbumin) from 22 SLE patients positive for anti-DNA antibodies and 85 hospitalized patients negative for anti-DNA antibodies were added to the wells and incubated overnight at 4° C. Human IgG bound to mAb1C7 was measured by adding alkaline phosphatase conjugated goat affinity purified antibodies specific for human gamma chains. Alkaline phosphatase was measured by the conversion of p-nitrophenylphosphate to p-nitrophenol at 405 nm. Positive responses were those greater than O.D=0.40, which corresponded to 2 S.D. above the mean for the 85 patients without serum anti-DNA antibodies by ELISA.

mab1C7 immobilized microtiter plates bound serum IgG from 13/22 (59.1%) clinically uncharacterized SLE patients with positive anti-DNA antibodies by ELISA compared to only 2/85 (2.4%) patients (including 36 with SLE) without measurable serum anti-DNA antibodies ($x^2$=42.1, p<0.001). In a separate study of serum from 87 patients with SLE who are clinically well 15 characterized, 14/45 (31%) the patients with anti-DNA antibodies have the DNAsp idiotype compared to only 1/42 without measureable anti-DNA antibodies ($x^2$=10.6, p=0.001). Moreover, the DNAsp idiotype was found in 9/18 patients with nephritis compared to only 9/69 patients without nephritis ($x^2$=12.9, p<0.001).

In order to determine the proportion of anti-DNA antibodies with the DNAsp idiotype, serum from SLE patients with anti-DNA antibodies and the DNAsp idiotype were absorbed with immobilized mAbIC7 and assayed for anti-DNA antibodies by ELISA; absorption of serum from 4 SLE patients with nephritis removed 22%, 29%, 35% and 57% of the anti-DNA antibody activity measured by ELISA compared to absorption with a control IgG 2a (mAb PP102). mAb1C7 anti-idiotype, therefore, 30 identified a conserved idiotype associated with anti-DNA antibodies in both murine and human lupus. Moreover, anti-DNA antibodies with the DNAsp idiotype were associated with nephritis in patients with SLE.

It is evident from the above results, that the probability of a disorder resulting from lupus nephritis can be detected by a positive result, using the antibodies according to the subject invention, while a negative result gives a substantial assurance of the absence of lupus nephritis. Specific anti-dsDNA may be used as an immunogen for vaccinating mammals for the production of antiidiotype antibodies specific for antibodies associated with lupus nephritis. Also, anti-DNA antibodies, namely antibodies to the anti-DNA idiotype, may be employed as drugs to reduce the level of anti-DNA antibodies associated with lupus nephritis which are present in a stricken host.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An anti-idiotypic antibody that
   a) binds specifically to antibodies that bind to ds DNA and
   b) does not bind to antibodies that do not bind to DNA.
2. The anti-idiotypic antibody of claim 1 wherein the anti-idiotypic antibody is a chimeric antibody.
3. The anti-idiotypic antibody of claim 1 wherein the anti-idiotypic antibody is a monoclonal antibody.
4. The hybridoma producing an anti-idiotypic monoclonal antibody of claim 3.
5. The monoclonal antibody 1C7.
6. The hybridoma producing 1C7.

* * * * *